(12) United States Patent
Ostrowski

(10) Patent No.: US 8,396,524 B2
(45) Date of Patent: Mar. 12, 2013

(54) MEDICAL SENSOR AND TECHNIQUE FOR USING THE SAME

(75) Inventor: Rafael Ostrowski, Pittsburg, CA (US)

(73) Assignee: Covidien LP, Mansfield, MA (US)

( * ) Notice: Subject to any disclaimer, the term of this patent is extended or adjusted under 35 U.S.C. 154(b) by 1138 days.

(21) Appl. No.: 11/528,292

(22) Filed: Sep. 27, 2006

(65) Prior Publication Data

US 2008/0076993 A1 Mar. 27, 2008

(51) Int. Cl.
*A61B 5/1455* (2006.01)
(52) U.S. Cl. .................... 600/310; 600/322
(58) Field of Classification Search .......... 600/310, 600/322, 323, 326; 356/39, 40, 41, 42
See application file for complete search history.

(56) References Cited

U.S. PATENT DOCUMENTS

| | | | |
|---|---|---|---|
| 2,136,236 A | 11/1938 | Draper | |
| 2,638,096 A | 5/1953 | Waldhaus | |
| 2,880,072 A | 3/1959 | Grosskopf | |
| 2,890,177 A | 6/1959 | Kilmer | |
| 2,904,033 A | 9/1959 | Shane | |
| 3,067,015 A | 12/1962 | Lawdermilt | |
| 3,068,073 A | 12/1962 | Stanford | |
| 3,113,842 A | 12/1963 | Udall | |
| 3,114,610 A | 12/1963 | Gafford et al. | |
| 3,238,020 A | 3/1966 | Eiseman | |
| 3,363,833 A | 1/1968 | Laerdal | |
| 3,373,735 A | 3/1968 | Gallagher | |
| 3,420,635 A | 1/1969 | Davis | |
| 3,467,601 A | 9/1969 | Brauer | |
| 3,505,022 A | 4/1970 | Luckey | |
| 3,507,623 A | 4/1970 | McConnaughey | |
| 3,556,122 A | 1/1971 | Laerdal | |
| 3,612,048 A | 10/1971 | Takaoka et al. | |
| 3,615,233 A | 10/1971 | Doering et al. | |
| 3,659,586 A | 5/1972 | Johns et al. | |
| 3,694,164 A | 9/1972 | Guenther | |
| 3,754,867 A | 8/1973 | Guenther | |
| 3,830,630 A | 8/1974 | Kiefer et al. | |
| 4,003,709 A | 1/1977 | Eaton et al. | |
| 4,019,862 A | 4/1977 | Dahms | |
| 4,077,404 A | 3/1978 | Elam | |
| 4,106,502 A | 8/1978 | Wilson | |

(Continued)

FOREIGN PATENT DOCUMENTS

| | | |
|---|---|---|
| DE | 1 007 525 | 5/1957 |
| EP | 0 477 501 A | 4/1992 |

(Continued)

OTHER PUBLICATIONS

Andrew J. Berger et al.; "Aqueous Dissolved Gas Measurements Using Near-Infrared Raman Spectroscopy"; Applied Spectroscopy, vol. 49, No. 8; pp. 1164-1169 (1995).

(Continued)

*Primary Examiner* — Eric Winakur
*Assistant Examiner* — Etsub Berhanu
(74) *Attorney, Agent, or Firm* — Fletcher Yoder

(57) ABSTRACT

A sensor is provided that is appropriate for optical detection of dissolved carbon dioxide. Such a sensor may be used for transcutaneous detection of carbon dioxide in the tissue. Alternatively, such sensors may be inserted into the tissue. Detection of dissolved carbon dioxide in the tissue may serve as a useful clinical marker for physicians.

26 Claims, 6 Drawing Sheets

U.S. PATENT DOCUMENTS

| | | | |
|---|---|---|---|
| 4,144,306 A | 3/1979 | Figueras | |
| 4,223,680 A | 9/1980 | Jobsis | |
| 4,277,251 A | 7/1981 | Leichnitz | |
| 4,287,153 A | 9/1981 | Towsend | |
| 4,321,930 A | 3/1982 | Jobsis et al. | |
| 4,332,771 A | 6/1982 | Leichnitz | |
| 4,346,584 A | 8/1982 | Boehringer | |
| 4,366,821 A | 1/1983 | Wittmaier et al. | |
| 4,380,240 A | 4/1983 | Jobsis et al. | |
| 4,389,372 A | 6/1983 | Lalin | |
| 4,438,067 A | 3/1984 | Siddiqi | |
| 4,509,522 A * | 4/1985 | Manuccia et al. | 600/326 |
| 4,548,906 A | 10/1985 | Sekikawa et al. | |
| 4,557,900 A | 12/1985 | Heitzmann | |
| 4,557,901 A | 12/1985 | Koyama et al. | |
| 4,691,701 A | 9/1987 | Williams | |
| 4,728,499 A | 3/1988 | Fehder | |
| 4,734,125 A | 3/1988 | Gehring et al. | |
| 4,774,941 A | 10/1988 | Cook | |
| 4,780,411 A | 10/1988 | Piejko et al. | |
| 4,788,153 A | 11/1988 | Detwiler et al. | |
| 4,790,327 A | 12/1988 | Despotis | |
| 4,805,623 A | 2/1989 | Jobsis | |
| 4,824,640 A | 4/1989 | Hildenbrand et al. | |
| 4,879,999 A | 11/1989 | Leiman et al. | |
| 4,928,687 A | 5/1990 | Lampotang et al. | |
| 4,945,918 A | 8/1990 | Abernathy | |
| 4,994,117 A | 2/1991 | Fehder | |
| 4,999,306 A | 3/1991 | Yafuso et al. | |
| 5,005,572 A | 4/1991 | Raemer et al. | |
| 5,057,695 A * | 10/1991 | Hirao et al. | 250/575 |
| 5,058,588 A * | 10/1991 | Kaestle | 600/323 |
| 5,109,840 A | 5/1992 | Daleiden | |
| 5,119,815 A | 6/1992 | Chance | |
| 5,124,129 A | 6/1992 | Riccitelli et al. | |
| 5,156,159 A | 10/1992 | Lampotang et al. | |
| 5,166,075 A | 11/1992 | Fehder | |
| 5,179,002 A | 1/1993 | Fehder | |
| 5,197,464 A | 3/1993 | Babb et al. | |
| 5,279,289 A | 1/1994 | Kirk | |
| 5,291,879 A | 3/1994 | Babb et al. | |
| 5,322,612 A | 6/1994 | Abe et al. | |
| 5,375,592 A | 12/1994 | Kirk et al. | |
| 5,421,329 A | 6/1995 | Casciani et al. | |
| 5,456,249 A | 10/1995 | Kirk | |
| 5,468,451 A | 11/1995 | Gedeon | |
| 5,472,668 A | 12/1995 | Mills et al. | |
| 5,480,611 A | 1/1996 | Mills et al. | |
| 5,515,847 A * | 5/1996 | Braig et al. | 600/316 |
| 5,517,985 A | 5/1996 | Kirk et al. | |
| 5,520,997 A | 5/1996 | Pourahmady et al. | |
| 5,630,413 A | 5/1997 | Thomas et al. | |
| 5,634,426 A | 6/1997 | Tomlinson et al. | |
| 5,661,302 A | 8/1997 | Evans et al. | |
| 5,679,884 A | 10/1997 | Kirk | |
| 5,692,503 A | 12/1997 | Kuenstner | |
| 5,714,121 A | 2/1998 | Alderete et al. | |
| 5,749,358 A | 5/1998 | Good et al. | |
| 5,782,237 A | 7/1998 | Casciani et al. | |
| 5,783,110 A | 7/1998 | Verdicchio et al. | |
| 5,846,836 A | 12/1998 | Mallow | |
| 5,849,594 A | 12/1998 | Balderson et al. | |
| 5,879,294 A | 3/1999 | Anderson et al. | |
| 5,957,841 A * | 9/1999 | Maruo et al. | 600/316 |
| 6,049,727 A * | 4/2000 | Crothall | 600/310 |
| 6,055,447 A | 4/2000 | Weil et al. | |
| 6,058,933 A | 5/2000 | Good et al. | |
| 6,078,833 A | 6/2000 | Hueber | |
| 6,123,075 A | 9/2000 | Kirk | |
| 6,216,024 B1 | 4/2001 | Weil et al. | |
| 6,265,221 B1 | 7/2001 | Nilsson | |
| 6,272,363 B1 | 8/2001 | Casciani et al. | |
| 6,319,723 B1 | 11/2001 | Jeffers et al. | |
| 6,378,522 B1 | 4/2002 | Pagan | |
| 6,427,687 B1 | 8/2002 | Kirk | |
| 6,428,748 B1 | 8/2002 | Wallach | |
| 6,436,347 B1 | 8/2002 | Cedeon | |
| 6,502,573 B1 | 1/2003 | Ratner | |
| 6,576,474 B2 | 6/2003 | Wallach | |
| D478,522 S | 8/2003 | Geist | |
| 6,662,033 B2 | 12/2003 | Casciani et al. | |
| 6,677,159 B1 | 1/2004 | Mallow | |
| 6,709,403 B1 | 3/2004 | Ratner | |
| 6,711,425 B1 | 3/2004 | Reuss | |
| 6,929,008 B2 | 8/2005 | Geist | |
| 7,283,242 B2 | 10/2007 | Thornton | |
| 7,319,894 B2 | 1/2008 | Higgins | |
| 7,349,726 B2 | 3/2008 | Casciani et al. | |
| 7,376,454 B2 | 5/2008 | Casciani et al. | |
| 7,415,298 B2 | 8/2008 | Casciani et al. | |
| 2002/0058864 A1 * | 5/2002 | Mansfield et al. | 600/316 |
| 2002/0082489 A1 | 6/2002 | Casciani et al. | |
| 2003/0003593 A1 | 1/2003 | Wallach | |
| 2003/0133123 A1 | 7/2003 | Yeh | |
| 2003/0199095 A1 | 10/2003 | Yuyama et al. | |
| 2004/0065329 A1 | 4/2004 | Geist | |
| 2004/0184024 A1 | 9/2004 | Katura et al. | |
| 2004/0204639 A1 | 10/2004 | Casciani et al. | |
| 2005/0016543 A1 | 1/2005 | Geist | |
| 2005/0039751 A1 | 2/2005 | Pagan | |
| 2005/0070773 A1 | 3/2005 | Chin et al. | |
| 2005/0177035 A1 * | 8/2005 | Botvinick et al. | 600/347 |
| 2005/0197548 A1 * | 9/2005 | Dietiker | 600/323 |
| 2005/0240107 A1 | 10/2005 | Alfano et al. | |
| 2005/0277818 A1 | 12/2005 | Myers | |
| 2006/0058595 A1 | 3/2006 | Herrmann | |
| 2006/0063995 A1 | 3/2006 | Yodh et al. | |
| 2006/0195026 A1 | 8/2006 | Casciani et al. | |
| 2006/0195027 A1 | 8/2006 | Casciani et al. | |
| 2006/0211929 A1 | 9/2006 | Casciani et al. | |
| 2006/0276697 A1 * | 12/2006 | Demuth et al. | 600/322 |
| 2006/0276713 A1 * | 12/2006 | Maier | 600/473 |
| 2007/0055119 A1 * | 3/2007 | Lash et al. | 600/323 |
| 2007/0060809 A1 | 3/2007 | Higgins | |
| 2007/0078311 A1 | 4/2007 | Al-Ali et al. | |
| 2008/0108887 A1 | 5/2008 | Higgins | |

FOREIGN PATENT DOCUMENTS

| | | |
|---|---|---|
| EP | 0 481 719 A1 | 4/1992 |
| EP | 0 307 625 B1 | 4/1994 |
| EP | 0 257 916 A1 | 1/1995 |
| EP | 0 509 998 B1 | 1/1996 |
| EP | 0 451 719 B1 | 12/1996 |
| EP | 0 601 171 B1 | 9/1997 |
| EP | 0 592 632 B1 | 8/1999 |
| EP | 01 022 558 A2 | 7/2000 |
| EP | 1 022 558 A3 | 7/2000 |
| EP | 1 039 294 A2 | 9/2000 |
| EP | 1 039 294 A3 | 10/2000 |
| EP | 1 245 947 A1 | 10/2002 |
| EP | 1 266 944 A1 | 12/2002 |
| EP | 0 858 594 B1 | 4/2003 |
| EP | 1 327 874 A2 | 7/2003 |
| EP | 1 153 294 B1 | 10/2003 |
| EP | 0 943 093 B1 | 11/2003 |
| EP | 1491135 | 12/2004 |
| GB | 1 043 988 A | 9/1966 |
| JP | 07072081 A | 3/1995 |
| JP | 08145979 A | 6/1996 |
| JP | 08247997 A | 9/1996 |
| JP | 09318528 A | 12/1997 |
| JP | 10073560 A | 3/1998 |
| JP | 2003072857 A | 3/2003 |
| JP | 2004177247 A | 6/2004 |
| JP | 2005054048 A | 3/2005 |
| WO | WO 90/01695 A1 | 2/1990 |
| WO | WO 90/03819 A1 | 4/1990 |
| WO | WO 91/05252 A1 | 4/1991 |
| WO | WO 92/20404 A1 | 11/1992 |
| WO | WO 93/20431 A1 | 10/1993 |
| WO | WO 94/00756 A1 | 1/1994 |
| WO | WO9423643 | 10/1994 |
| WO | WO 96/19727 | 6/1996 |
| WO | WO 96/24054 A1 | 8/1996 |
| WO | WO 97/10496 A1 | 3/1997 |
| WO | WO 97/12227 A1 | 4/1997 |
| WO | WO 98/26283 A1 | 6/1998 |

| | | | |
|---|---|---|---|
| WO | WO 00/29830 A1 | 5/2000 |
| WO | WO 00/43778 A1 | 7/2000 |
| WO | WO 01/04624 A1 | 1/2001 |
| WO | WO 01/44385 A1 | 6/2001 |
| WO | WO 03/045608 A1 | 3/2003 |
| WO | WO 2004/077035 A1 | 9/2004 |
| WO | WO2007051066 | 5/2007 |

OTHER PUBLICATIONS

S. Schaden et al.; "Direct Determination of Carbon Dioxide in Aqueous Solution Using Mid-Infrared Quantum Cascade Lasers"; Applied Spectroscopy; vol. 58; No. 6, pp. 667-670 (2004).

Near IR Spectra of Carbon Dioxide in $H_2O$ posted on the company's web site . . . http://www.astrochem.org.CO2H2o.html.

J.A. Berman et al.; "The Einstein Carbon Dioxide Detector"; Anesthesiology, vol. 60, No. 6; pp. 613-614 (1984).

P.K. Birmingham et al.; "Esophageal Intubation: A Review of Detection Techniques"; Anesth. Analg.; vol. 65; pp. 886-891 (1986).

Current Projects CapnoProbe™ SL Monitoring System posted on the company's web site; Optical Sensors Incorporated | Projects . . . http://64.226.16.15/projects.htm Copyright 2003.

S.G.R.G. Barton et al.; "Expression of heat shock protein 32 (hemoxygenase-1) in the normal and inflamed human stomach and colon: an immunohistochemical study"; Cell Stress & Chaperones, vol. 8, No. 4; pp. 329-334 (2003).

Jessy Deshane et al.; "Heme oxygenase-1 expression in disease states"; Acta Biochimica Polonica, vol. 52, No. 2; pp. 273-284 (2005).

Shai Efrati, MD et al.; "Optimization of Endotracheal Tube Cuff Filling by Continuous Upper Airway Carbon Dioxide Monitoring"; Anesth. Analg; vol. 101, pp. 1081-1088 (2005).

Shai Efrati, MD; "Is Capnometry the Optimum Method for Assessing the Adequacy of Endotracheal Tube Cuff Seal?"; Anesthesia & Analgesia; vol. 103, No. 2; pp. 505-506 (Aug. 2006).

Shaw-Fang Yet et al.; "Heine Oxygenase 1 in Regulation of Inflammation and Oxidative Damage"; Methods in Enzymology; vol. 353, pp. 163-176 (2002).

\* cited by examiner

MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Physiological characteristics that physicians may desire to monitor include constituents of the blood and tissue, such as oxygen and carbon dioxide. For example, abnormal levels of carbon dioxide in the blood may be related to perfusion problems. Thus, assessment of carbon dioxide levels may be useful for diagnosing a variety of clinical states related to the circulation. Carbon dioxide and other blood constituents may be directly measured by taking a blood sample, or may be indirectly measured by assessing the concentration of those constituents in the tissue or respiratory gases. For example, carbon dioxide in the bloodstream equilibrates rapidly with carbon dioxide in the lungs, and the partial pressure of the carbon dioxide in the lungs approaches the amount in the blood during each breath. Accordingly, physicians often monitor respiratory gases during breathing in order to estimate the carbon dioxide levels in the blood.

However, estimation of carbon dioxide by respiratory gas analysis has certain disadvantages. It is often inconvenient to measure carbon dioxide in samples collected from an intubation tube or cannula. Although these methods are considered to be noninvasive, as the surface of the skin is not breached, the insertion of such devices may cause discomfort for the patient. Further, the insertion and operation of such devices also involves the assistance of skilled medical personnel.

Carbon dioxide in the blood that diffuses into the tissue may also be measured transcutaneously by sensors placed against a patient's skin. While these sensors are easier to use than respiratory gas sensors, they also are associated with certain disadvantages. For example, these sensors may operate by capturing a volume of carbon dioxide gas as it dissolves out of the skin. Thus, such sensors may involve a certain time delay before a sufficient gas volume has been captured. Other such sensors may operate by measuring carbon dioxide that diffuses into mucosal secretions. However, such secretions may also contain trace amounts of carbon dioxide from the environment, which may interfere with tissue carbon dioxide measurements.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a sensor that includes: a sensor body adapted for use associated with a patient's tissue; an emitter disposed on the sensor body, wherein the emitter is adapted to emit at least one wavelength of light between 4200 nm and 4350 nm; and a detector disposed on the sensor body, wherein the detector is adapted to detect the wavelength of light, and wherein the emitter and the detector are adapted to have an optical distance of 200 micrometers or less.

There is provided a system that includes: a monitor; and a sensor adapted to be coupled to the monitor, the sensor including: a sensor body adapted for use associated with a patient's tissue; an emitter disposed on the sensor body, wherein the emitter is adapted to emit at least one wavelength of light between 4200 nm and 4350 nm; and a detector disposed on the sensor body, wherein the detector is adapted to detect the wavelength of light, and wherein the emitter and the detector are adapted to have an optical distance of 200 micrometers or less.

There is provided a method of calculating dissolved carbon dioxide that includes: emitting a light between 4200 nm and 4350 nm into a tissue with an emitter; detecting the light with a detector that is 200 micrometers or less from the emitter; sending a signal related to the detected light to a processor; and determining a concentration of dissolved carbon dioxide in the tissue There is provided a method of manufacturing a sensor that includes: providing a sensor body adapted for use associated with a patient's tissue; providing an emitter disposed on the sensor body, wherein the emitter is adapted to emit at least one wavelength of light between 4200 nm and 4350 nm; and providing a detector disposed on the sensor body, wherein the detector is adapted to detect the wavelength of light, and wherein the emitter and the detector are adapted to have an optical distance of 200 micrometers or less.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A sensor and/or sensing system is provided herein that may assess a tissue constituent content with a sensing component that is adapted to provide an optical signal related to the tissue constituent. For example, carbon dioxide and other constituents in the bloodstream may diffuse into the tissue and may dissolve into the tissue cells and the interstitial fluid. Thus, the levels of dissolved carbon dioxide in the tissue may serve as a surrogate marker for carbon dioxide levels in the bloodstream. Carbon dioxide levels in the tissue and/or bloodstream may be useful in assessing a variety of clinical states.

A sensor according to the present techniques placed proximate to and/or slightly beneath a tissue surface may optically sense and measure carbon dioxide that is still diffused, i.e. dissolved, in the tissue. Such a sensor may provide a noninvasive or minimally invasive technique for determining levels of dissolved carbon dioxide in the tissue. Further, the spectroscopic sensors herein provide a relatively low-noise, low-artifact signal that may be easily processed with minimal filtering in order to provide information related to dissolved carbon dioxide in the tissue.

Figure 1:
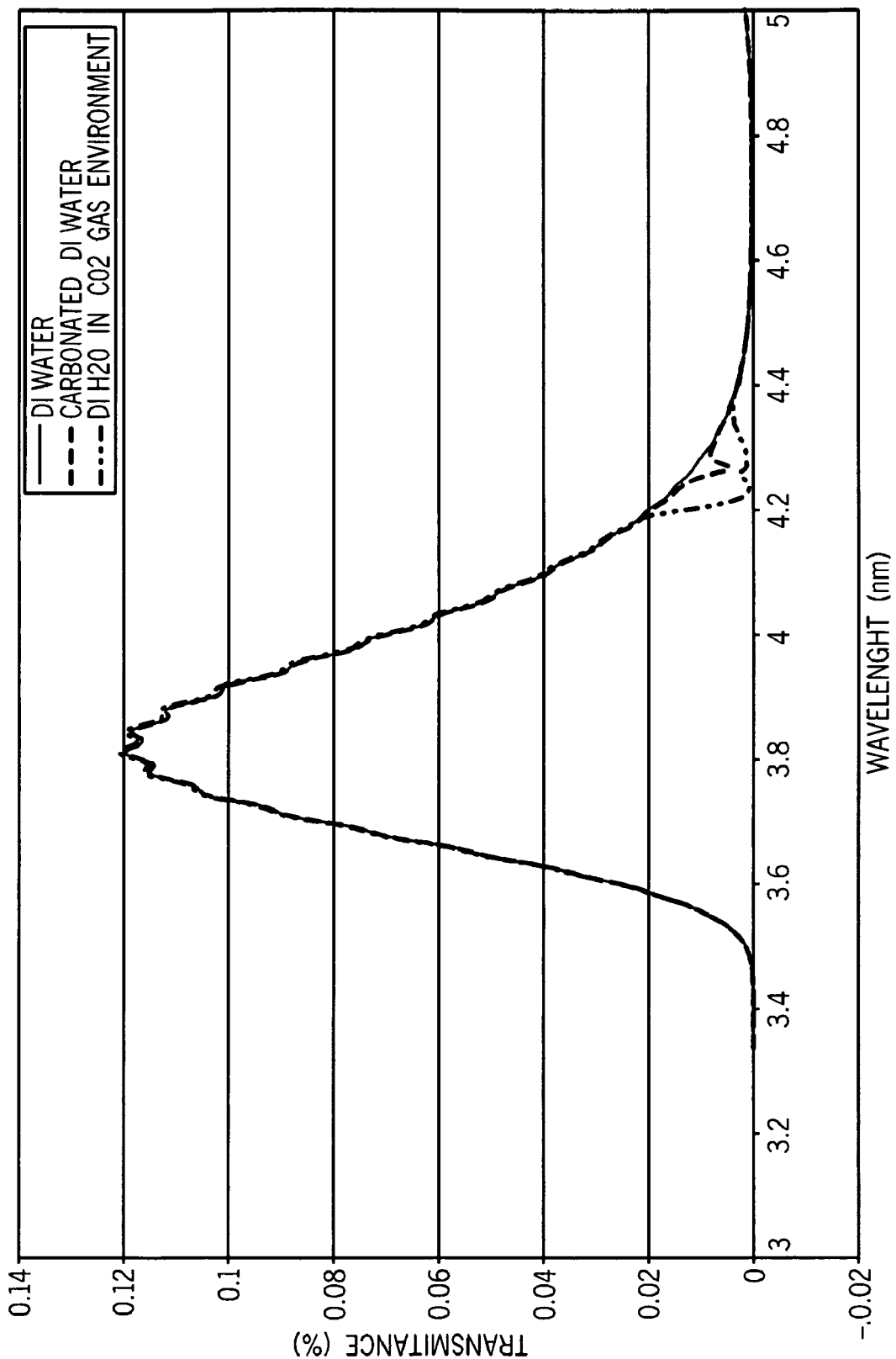
FIG. 1 is a graph of the infrared spectra of dissolved carbon dioxide.

Sensors as provided herein may spectroscopically distinguish dissolved carbon dioxide from other tissue constituents, including water, at unique wavelengths in the infrared spectrum. FIG. 1 depicts the absorption spectra of water, carbonated water, and water in a gaseous carbon dioxide environment. As depicted, gaseous carbon dioxide exhibits vibration in the mid infrared region of the spectrum with a doublet peak centered around 4340 nm that is distinguishable from water absorption at this wavelength. Further, carbon dioxide dissolved in liquid vibrates as a singlet peak that is sharper than the gaseous carbon dioxide doublet peak and is also distinguishable from water absorption. The dissolved carbon dioxide singlet absorption peak is centered generally about 4267 nm. As the carbon dioxide that is present in the tissue is almost completely in the form of dissolved carbon dioxide, the contribution of gaseous carbon dioxide to any tissue measurement may be negligible. Thus, in order to determine the concentration of dissolved carbon dioxide, wavelengths between 4200 nm and 4350 nm may be used to spectroscopically probe a tissue of interest and distinguish carbon dioxide from water or other tissue constituents.

Generally, it is envisioned that sensors according to the present techniques are appropriate for use in determining the presence or levels of tissue constituents in a variety of tissues. The sensor may be placed against the tissue, either manually, mechanically, adhesively, or otherwise. The sensors provided herein may be used on any appropriate patient skin surface or tissue, including mucosal and nonmucosal tissues. For example, a sensor may be used in the upper respiratory tract or the gastrointestinal tissue, including the oral and nasal passages. These passages may include the tongue, the floor of the mouth, the roof of the mouth, the soft palate, the cheeks, the gums, the lips, the esophagus and any other respiratory or gastrointestinal tissue. Further, a sensor as described herein is appropriate for use adjacent to or proximate to any mucosal surface, i.e., patient surfaces that include a mucous membrane or surfaces that are associated with mucus production. In addition to the respiratory tract, mucosal surfaces may include vaginal, rectal, or gastrointestinal surfaces. Sensors as provided herein may also be used to assess carbon dioxide in a patient internal organ. Other appropriate sensor placement sites may include a patient's digit or forehead.

Sensors as provided by the present techniques may be disposable, reusable, or partially disposable. In addition, the sensors may be appropriate for short-term or for longer-term monitoring. When used for long-term monitoring, the sensor may be applied to the patient's tissue either by mechanical clamping or by a suitable adhesive, such as a mucoadhesive, or by any other suitable holding device, such as a clip. Further, the sensors provided herein may be used in conjunction with any suitable medical device, including a catheter, an endotracheal tube, a stent, a probe, a feeding tube, or an intravenous tube.

Figure 2:
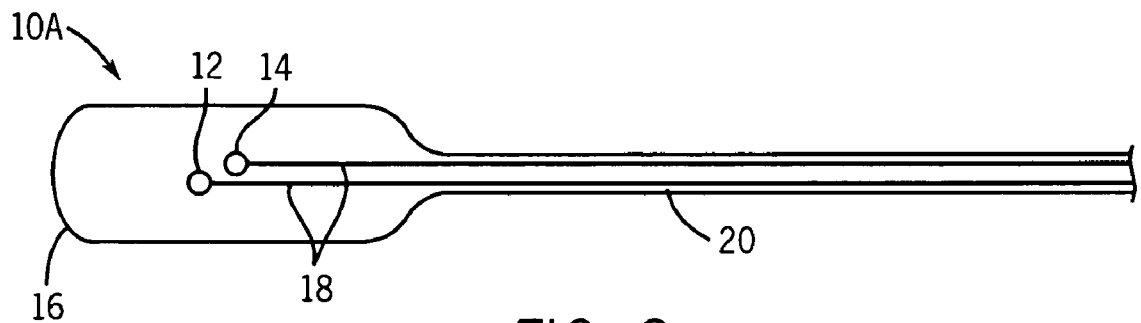
FIG. 2 illustrates a perspective view sensor for detection of carbon dioxide according to the present invention.

An exemplary sensor 10A appropriate for use for assessing dissolved carbon dioxide in the tissue is shown in FIG. 2. FIG. 2 illustrates an exemplary reflectance-type bandage sensor appropriate for use on a patient digit. The sensor 10A may have an emitter 12 and a detector 14 disposed on a sensor body 16, which may be made of any suitable material, such as polymers, foam, woven material, or paper. In the depicted embodiment, the emitter 12 and a detector 14 are coupled to a cable 20 by a pair of wire leads 18 that are responsible for transmitting electrical and/or optical signals to and from the emitter 12 and detector 14 of the sensor 10A. The cable 20 may be permanently coupled to the sensor 10A, or it may be removably coupled to the sensor 10A—the latter alternative being more useful and cost efficient in situations where the sensor 10A is disposable.

As depicted, the sensor 10A is reflectance-type sensor that may operate by emitting light into the tissue and detecting the light that is transmitted and scattered by the tissue. Accordingly, the emitter 12 and detector 14 are typically placed on the same side of the sensor site. For example, a reflectance type sensor may be placed on a patient's fingertip or forehead such that the emitter 12 and detector 14 lie side-by-side. Reflectance type sensors detect light photons that are scattered back to the detector 14. A sensor 10 may also be a "transflectance" sensor, such as a sensor that may subtend a portion of a baby's heel. During operation, the emitter 12 shines one or more wavelengths of light through the sensor site and the light received by the detector 14 is processed to determine various physiological characteristics of the patient, such as the amount of dissolved carbon dioxide in the tissue. In each of the embodiments discussed herein, it should be understood that the locations of the emitter 12 and the detector 14 may be exchanged. In either arrangement, the sensor will perform in substantially the same manner.

Figure 3:
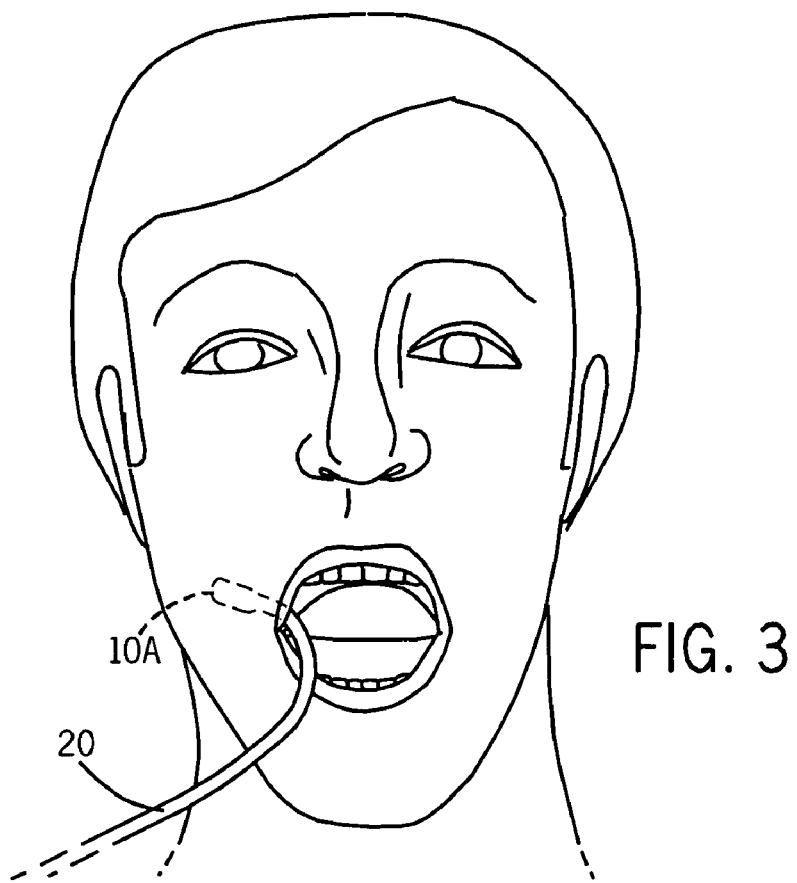
FIG. 3 illustrates a patient using the sensor of FIG. 2.

FIG. 3 illustrates the placement of the sensor 10A on a buccal surface in order to assess carbon dioxide dissolved in the tissue or interstitial fluid. The sensor 10A may be inserted into the oral passage and placed adjacent to a mucosal tissue. The sensor 10A may be suitably sized and shaped such that a patient may easily close his or her mouth around the cable 20 with minimal discomfort. The sensor 10A may be adapted to be held against the cheek or any other mucosal tissue. Because the mucosal tissue is an aqueous environment, in certain embodiments, a sensor 10A may include materials that function as a barrier layer that are hydrophobic or otherwise water-resistant. For example, a barrier layer may form a contact surface of the sensor 10A that prevents water from entering the sensor 10A and interfering with the sensing components. If such a barrier is disposed on the sensor such that the emitter 12 and the detector 14 are substantially covered, the barrier should be optically transparent to the wavelengths emitted by the emitter 12. Suitable materials include polymers, such as polytetrafluoroethylene (PTFE). Other suitable materials include microporous polymer films, such as those available from the Landec Corporation (Menlo Park, Calif.).

Figure 4:
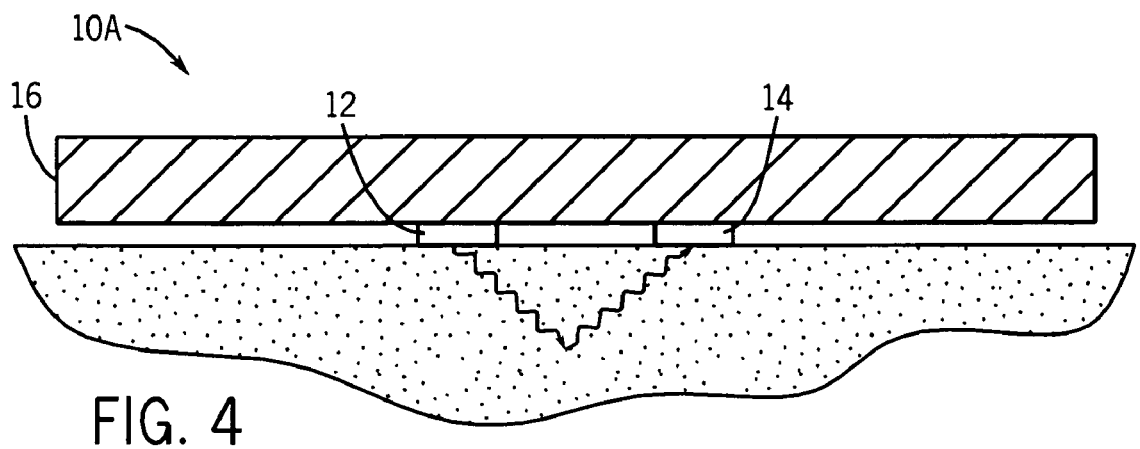
FIG. 4 is a cross-sectional view of the sensor of FIG. 2 applied to a patient.

A cross-sectional view of the sensor 10A is shown in FIG. 4. The sensor body 16 is formed to provide a surface that is suitably shaped to be secured against a mucosal tissue 18. In order to capture carbon dioxide measurements in the infrared range while avoiding interference from water absorption, the emitter 12 and detector 14 typically may have an optical distance of 200 micrometers or less. Because light in the infrared range is very strongly absorbed by water in the tissue, using a small optical distance prevents the light originating from the emitter 12 from being completely absorbed by water in the tissue prior to reaching the detector 14. The longer the optical distance (i.e. the greater the distance that the light travels through the tissue), the smaller the optical signal that reaches the detector 14, until the optical distance reaches a certain length threshold at which point substantially none of the emitted light reaches the detector 14. Thus, by limiting the distance that the light travels, the signal related to the dissolved carbon dioxide is generally preserved. The contribution of water absorption to the total absorption may be subtracted by a downstream medical device, discussed below.

Because the sensor 10A is in a reflectance configuration, the light originating from the emitter 12 first travels into the tissue and is refracted before impinging on the detector 14. For reflectance sensors, the light that passes through the tissue and is related to the carbon dioxide levels does not travel directly from the emitter 12 to the detector 14 by the shortest geometric path, but instead travels in a substantially V-shaped configuration through the tissue, as indicated schematically in FIG. 4. The optical distance for such a configuration is the geometric length of the V-shaped path the light follows from the emitter 12 to the detector 14. In order to have an optical distance of 200 micrometers or less, the emitter 12 and detector 14 may be placed less than 100 micrometers apart on the sensor body 16.

In a "transmission type sensor" the emitter 12 and detector 14 are typically placed on opposing sides of the sensor site. As noted above, the positions of the emitter 12 and the detector 14 may be exchanged in a transmission type sensor. The optical distance between the emitter 12 and the detector 14 in a transmission type sensor is the shortest geometric path between them. Thus, in order to maintain an optical distance of 200 micrometers or less, the emitter 12 and detector 14 should be 200 micrometers or less apart.

Figure 5:
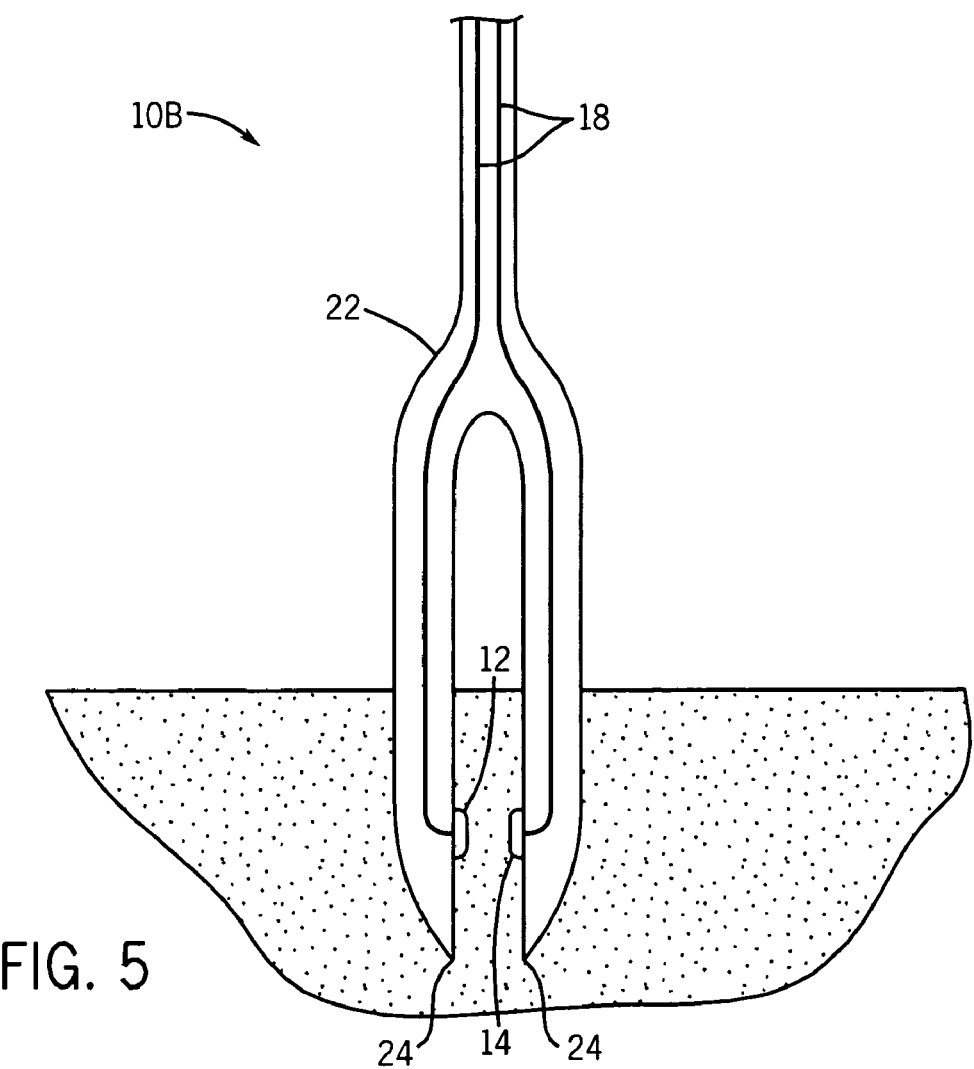
FIG. 5 illustrates an alternative embodiment of a transmission-type microneedle sensor according to the present techniques.

An exemplary transmission type sensor 10B is shown in FIG. 5. As a transmission type sensor generally holds tissue between the emitter 12 and detector 14, the sensor body 22 may assume a configuration similar to a two-tined prong that may be inserted a small distance into the tissue. The tines 24 may be pointed or sharp to facilitate insertion into the skin. Generally, in order to maintain a substantially fixed optical distance between the emitter 12 and detector 14, the tines 24 may be made of a substantially rigid material, such as a metal or plastic. The tines may be suitably sized and shaped to accommodate an emitter 12, detector 14, and leads 18 that may carry signals to and/or from the sensing components. In an alternative configuration (not shown), the sensor 10B may be configured like a caliper in order to pinch a sufficiently small amount of skin between the emitter 12 and detector 14 to maintain a suitable optical distance between them. Such a configuration may avoid insertion of the sensor 10B into the skin.

In a specific embodiment, it may be advantageous to use fiber optic sensing elements coupled to the emitter 12 and the detector 14 because they may be configured to have very small optical distances. Thus, the emitter 12 and detector 14 may be in the configuration of a fiber optic bundle with multiple emitting and detecting fibers that are configured to shine light into the tissue. Fiber optic sensing elements may be used on the surface of the skin or in a minimally structure, such as a microneedle, discussed below. Fiber optic sensing elements may be conventional optical fibers having a light transmitting fiber core that is transparent in the mid-infrared range, such as a silver halide, chalcogenide, or fluoride fiber (available from IR Photonics). The fibers may also include a cladding layer (not shown) for preventing or restricting transmission of light radially out of the core, and a protective outer or buffer layer (also not shown). The emitter 12 may also include coupling optics, such as a microscope objective lens, for transmitting light into the fiber. The separation distance between emitting fibers and the detecting fibers may be up to 200 micrometers. Such an arrangement may be achieved by using optical fibers with diameters of up to 200 micrometers.

Figure 6:
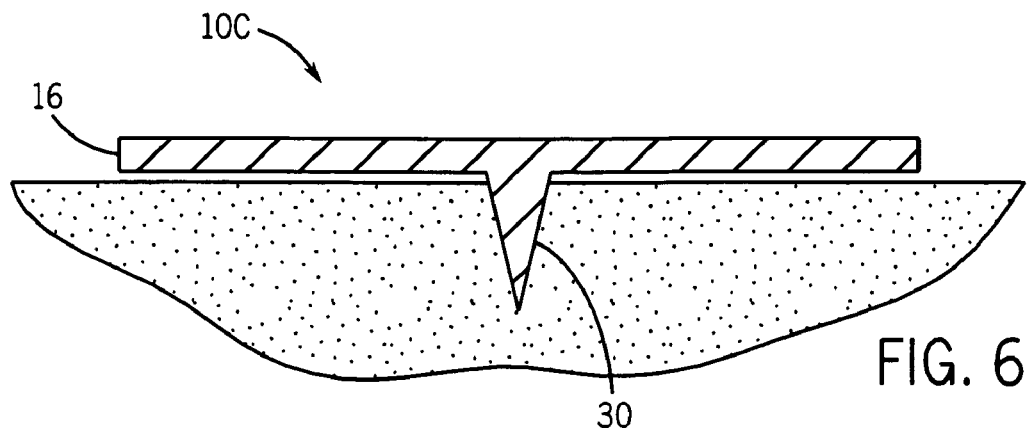
FIG. 6 illustrates an exemplary fiber optic microneedle sensor according to the present techniques.
Figure 7:
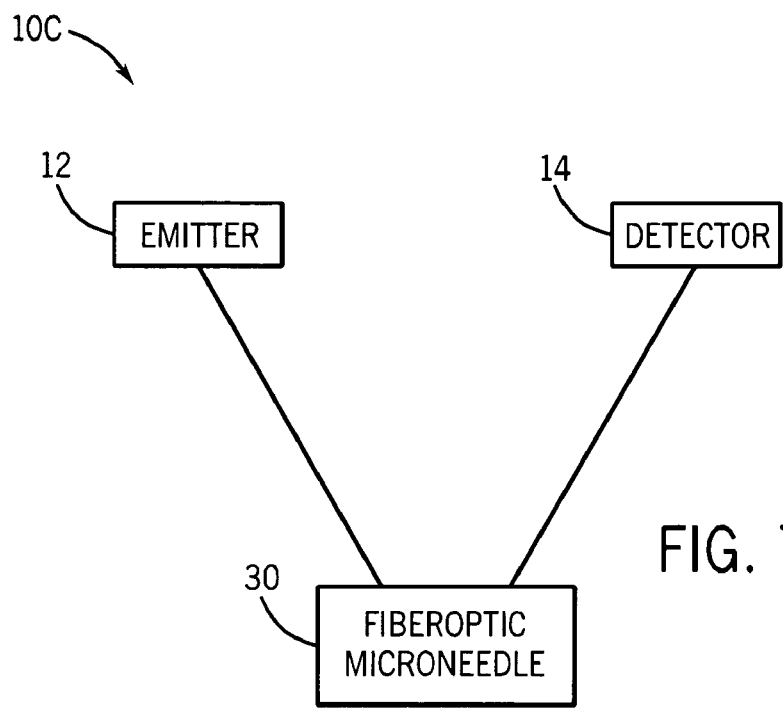
FIG. 7 is a block diagram of the fiber optic microneedle of FIG. 6.

Alternatively, a sensor may include a microneedle structure to allow minimally invasive insertion of a sensor into the skin. FIGS. 6 and 7 illustrate an exemplary fiber optic sensor 10C. The sensor body 16 includes a fiber optic microneedle 30 that may be inserted a short distance into a patient's tissue. As illustrated in FIG. 7, one end of the fiber optic microneedle 30 is connected to an emitter 12. The microneedle 30 is also connected to a detector 14 for detecting the light transmitted through the microneedle 30. The separation distance between emitting fiber and the detecting fiber may be up to 200 micrometers. Such an arrangement may be achieved by using optical fibers with diameters of up to 200 micrometers. Such a configuration may provide the advantage of a small, minimally invasive structure that may pierce through the tough outer layers of a patient's epidermis to access the perfused dermal tissue beneath the epidermis in order to assess the carbon dioxide levels. The microneedle 30 may thus be sufficiently long to traverse the epidermis. The sensor 10C may be advantageous for use on both mucosal and nonmucosal tissue.

Figure 8:
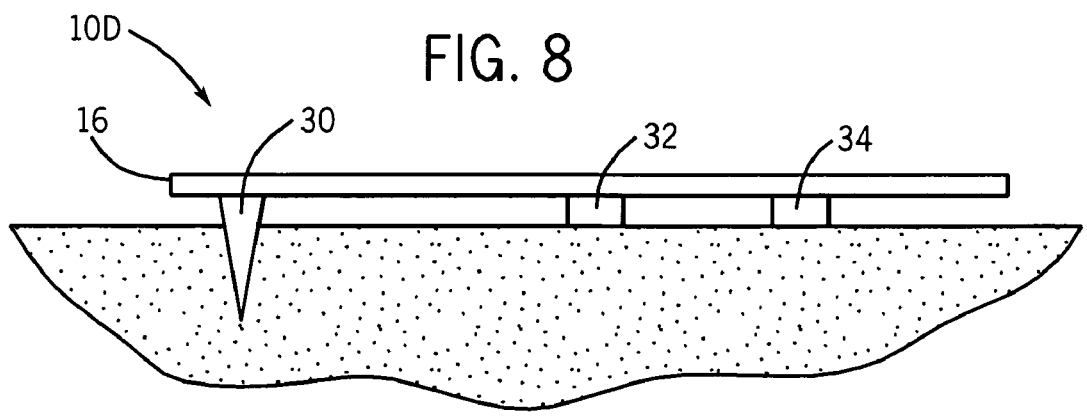
FIG. 8 illustrates an alternate embodiment of a fiber optic microneedle sensor that also includes optical elements for pulse oximetry sensing.

In an alternative embodiment, a dual-function sensor 10D is depicted in FIG. 8 that includes a secondary emitter 32 and a secondary detector 34 in addition to a microneedle 30. Such a sensor 10D may simultaneously assess different physiological constituents. For example, the secondary emitter 32 and the secondary detector 34 may be adapted assess a blood oxygen level while the microneedle 30 is adapted to assess dissolved carbon dioxide. Alternatively (not shown), the microneedle 30 may also include secondary emitters and detectors that are adapted to emit and detect light that is related to a blood oxygen level.

Figure 9:
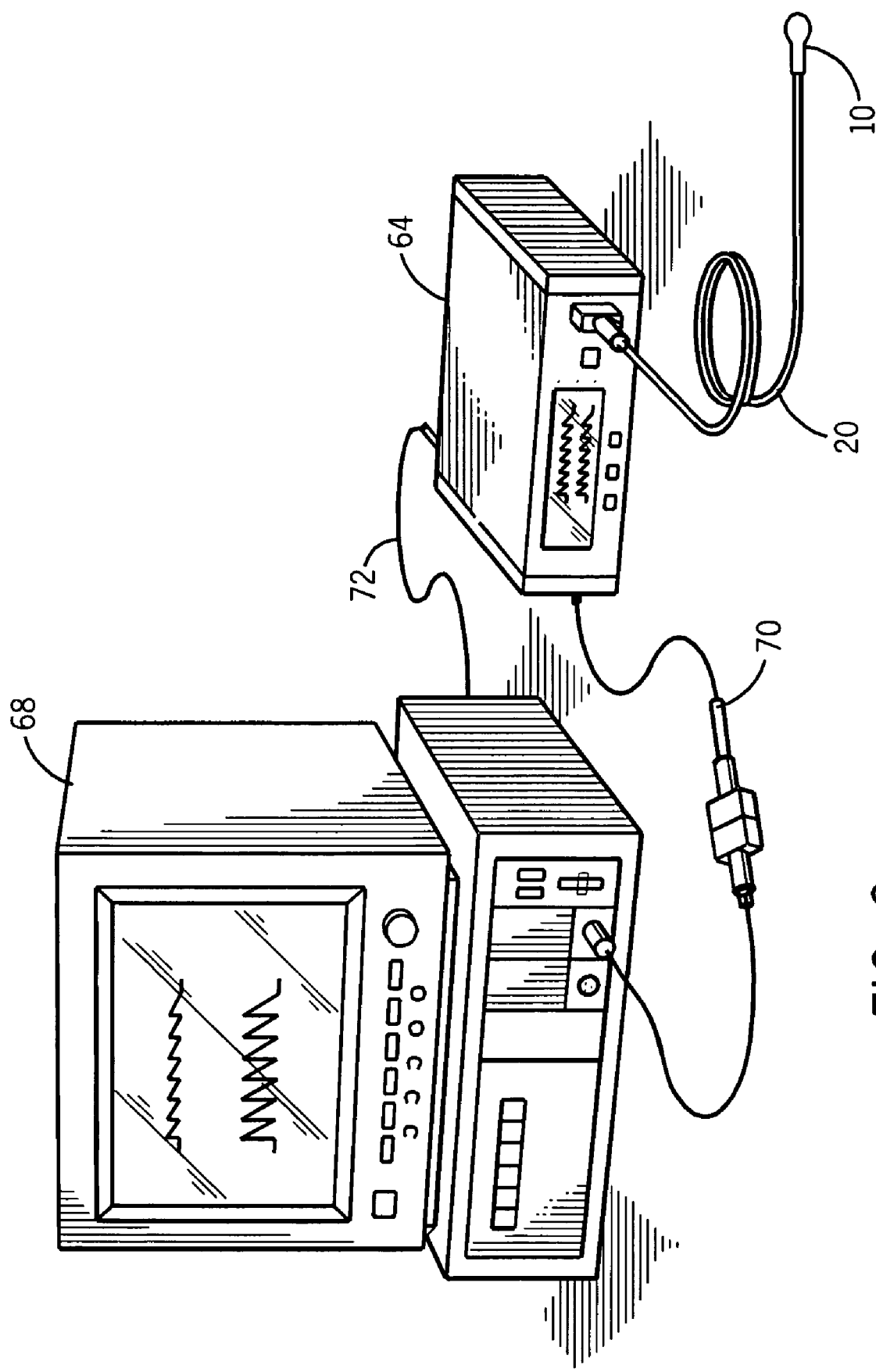
FIG. 9 illustrates a physiological constituent detection system coupled to a multi-parameter patient monitor and a sensor according to embodiments of the present invention.

The exemplary sensors, described here generically as a sensor 10, may be coupled to a monitor 64 that may display the concentration of tissue constituents as shown in FIG. 9. It should be appreciated that the cable 20 of the sensor 10 may be coupled to the monitor 64 or it may be coupled to a transmission device (not shown) to facilitate wireless transmission between the sensor 10 and the monitor 64. The monitor 64 may be any suitable monitor 64, such as those available from Nellcor Puritan Bennett, Inc. Furthermore, to upgrade conventional tissue constituent detection provided by the monitor 64 to provide additional functions, the monitor 64 may be coupled to a multi-parameter patient monitor 68 via a cable 70 connected to a sensor input port or via a cable 72 connected to a digital communication port.

In certain embodiments, the sensing component may include optical components, e.g. an emitter 12 and detector 14 pair that may be of any suitable type. For example, the emitter 12 may be one or more light emitting diodes adapted to transmit one or more wavelengths of light in the mid-infrared range, and the detector 14 may one or more photodetectors selected to receive light in the range or ranges emitted from the emitter. Alternatively, an emitter may also be a laser diode or a vertical cavity surface emitting laser (VCSEL). An emitter 12 and detector 14 may also include optical fiber sensing components. An emitter 12 may include a broadband or "white light" source, in which case the detector 14 could include any of a variety of elements for selecting specific wavelengths, for example reflective or refractive elements or interferometers. These kinds of emitters 12 and/or detectors 14 would typically be coupled to the rigid or rigidified sensor 10 via fiber optics. Alternatively, a sensor 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

Figure 10:
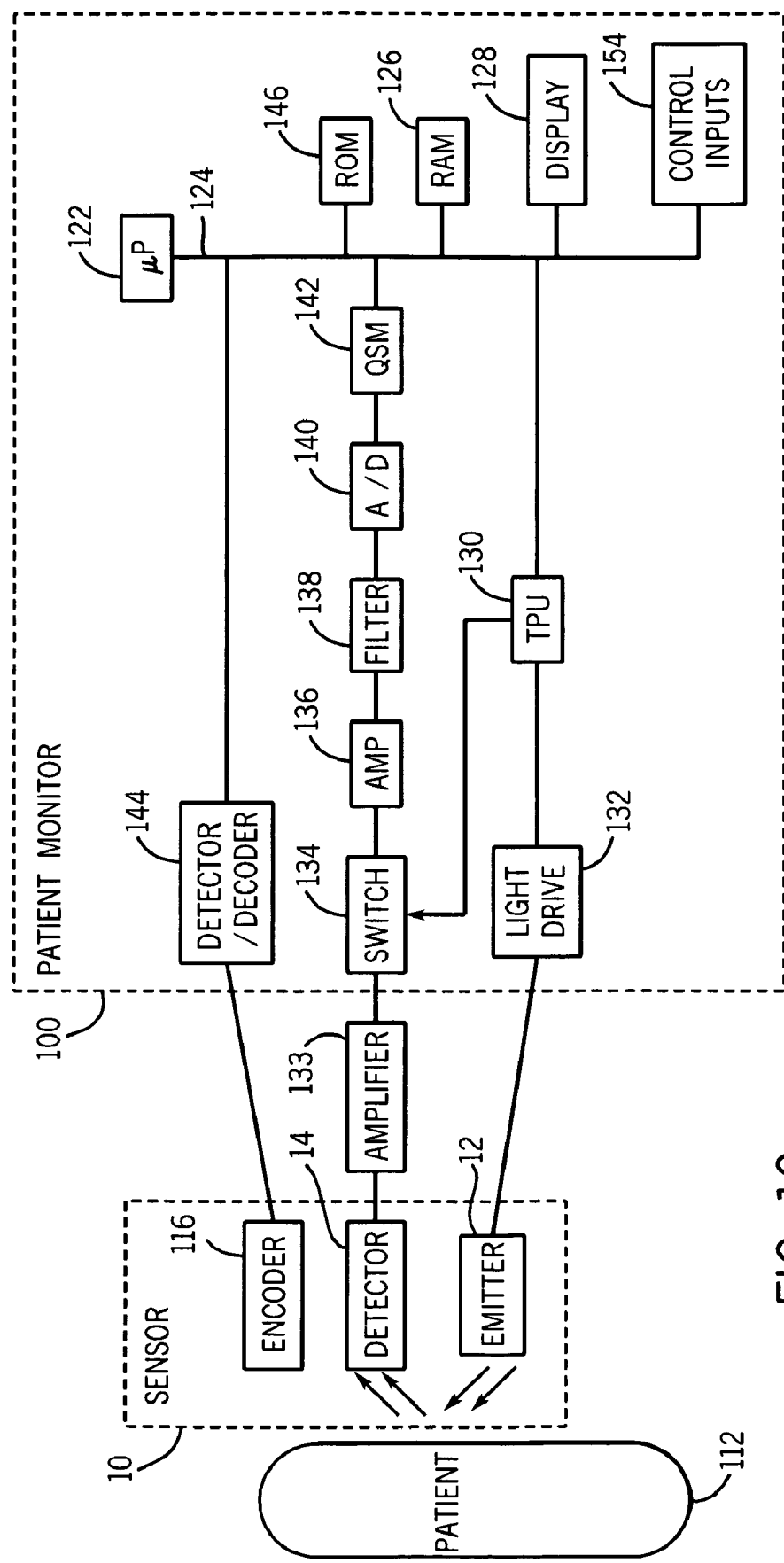
FIG. 10 is a block diagram of the sensor and physiological constituent detection system.

FIG. 10 is a block diagram of one embodiment of a patient monitor 100 that may be configured to implement the embodiments of the present invention. Light from emitter 12 passes into a blood perfused tissue 112, and is scattered and detected by detector 14. The sensor 10 is connected to a patient monitor 100. The monitor 100 includes a microprocessor 122 connected to an internal bus 124. Also connected to the bus are a RAM memory 126 and a display 128. A time processing unit (TPU) 130 provides timing control signals to light drive circuitry 132 which controls when the emitter 12 is illuminated, and if multiple light sources are used, the multiplexed timing for the different light sources. TPU 130 also controls the gating-in of signals from detector 14 through an amplifier 133 and a switching circuit 134. These signals are sampled at the proper time, depending upon which of multiple light sources is illuminated, if multiple light sources are used. The received signal from the detector 14 and the contact sensor 10 may be passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier, filter and A/D converters for multiple light wavelengths or spectra received.

A sensor 10 containing an emitter 12 and a detector 14 may also contain an encoder 116 that provides signals indicative of the wavelength of light source 12 to allow the monitor to select appropriate calibration coefficients for calculating dissolved carbon dioxide concentration. The encoder 116 may, for instance, be a coded resistor, EEPROM or other coding devices (such as a capacitor, inductor, PROM, RFID, a bar-code, parallel resonant circuits, or a colorimetric indicator) that may provide a signal through detector/decoder 144 to the processor 122 related to the characteristics of the sensor 10 that may allow the processor 122 to determine the appropriate calibration characteristics for the sensor 10. Further, the encoder 116 may include encryption coding that prevents a disposable part of the sensor 10 from being recognized by a detector/decoder 144 and processor 122 that are not able to decode the encryption. Such encryption coding is described in U.S. Pat. No. 6,708,049, which is hereby incorporated by reference in its entirety.

Based on the value of the received signals corresponding to the light received by detector 14, microprocessor 122 will calculate the carbon dioxide concentration using various algorithms. These algorithms utilize coefficients, which may be empirically determined, corresponding to, for example, the wavelengths of light used. These are stored in a ROM 146. In a two-wavelength system, the particular set of coefficients chosen for any pair of wavelength spectra is determined by the value indicated by the encoder 116 corresponding to a particular light source in a particular sensor 10. For example, the first wavelength may be a carbon dioxide signal wavelength, and the second wavelength may be a water correction wavelength. In one embodiment, multiple resistor values may be assigned to select different sets of coefficients. In another embodiment, the same resistors are used to select from among the coefficients appropriate for an infrared source paired with either a near red source or far red source. The selection between whether the wavelength sets can be selected with a control input from control inputs 154. Control inputs 154 may be, for instance, a switch on the monitor, a keyboard, or a port providing instructions from a remote host computer. Furthermore, any number of methods or algorithms may be used to determine carbon dioxide levels, oxygen saturation or any other desired physiological parameter.

The monitor 100 may be configured to receive signals from the sensor 10 related to a physiological constituent in order to calculate a calibrated carbon dioxide. For example, the emitter 12 may include one or more emitters configured to emit a reference wavelength useful for calculating the effects of light absorption not related to dissolved carbon dioxide in the tissue. At mid infrared wavelengths, the contribution of water to the total absorption may be calculated and corrected by using a reference wavelength. For example, water absorption, such as at wavelengths between 3500 nm-4100 nm or 4400 nm-4500 nm, may be used as a reference to calculate the total contribution of water absorption to the spectrum. Alternatively, a spectral difference may be calculated using a control such as pure water in order to subtract the spectral contribution of water. Although dissolved carbon dioxide absorption may be distinguished from water absorption at certain mid infrared wavelengths, in certain embodiments, it may be advantageous to correct for the contribution of water absorption to the total absorption in order to obtain a corrected absorption for dissolved carbon dioxide. In other embodiments, it may be advantageous to use hemoglobin absorption as a reference, either instead of or in addition to a water reference. Hemoglobin absorption may be in the 600-1100 nm range. After calculating a calibrated carbon dioxide level, a processor 122 may instruct the display 128 to display a message related to the carbon dioxide levels. The message may be a numerical carbon dioxide level. Additionally, a message may include an audio and/or visual alarm if the carbon dioxide level is greater than or less than an empirically determined threshold. A message may also be a text indicator, such as "CARBON DIOXIDE WITHIN NORMAL RANGE."

Further, the monitor 100 may be configured to receive information about the ambient environment of the sensor 10 from environmental sensors (not shown). Such information may be processed by the processor 122 and may be useful for correcting the carbon dioxide calibration curves for a particular patient. Examples of environmental sensors that may provide information that may be incorporated into a carbon dioxide level calculation include patient temperature sensors, skin pH sensors, atmospheric pressure sensors, and carbon dioxide partial pressure sensors.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other tissue and/or blood constituents. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of carbon dioxide concentration in the tissue, the sensors fabricated using the present method may be used to evaluate any number of sample types in a variety of industries, including fermentation technology, cell culture, and other biotechnology applications.

What is claimed is:

1. A dissolved carbon dioxide sensor comprising:
a sensor body adapted for use associated with a patient's tissue;
one or more emitters disposed on the sensor body, wherein each emitter is adapted to emit at least one wavelength of light between 4200 nm and 4350 nm; and
one or more detectors disposed on the sensor body, wherein each detector is adapted to detect the wavelength of light and generate a signal correlated with a level of dissolved carbon dioxide in the patient's tissue, wherein each detector is positioned to have an optical distance of 200 micrometers or less with respect to at least one emitter, and wherein there are no other detectors that detect the wavelength of light disposed on the sensor body that do not have the optical distance of 200 micrometers or less with respect to at least one emitter.

2. The sensor, as set forth in claim 1, wherein each emitter comprises at least one light emitting diode.

3. The sensor, as set forth in claim 1, wherein each detector comprises at least one photodetector.

4. The sensor, as set forth in claim 1, wherein the at least one wavelength of light is 4327 nanometers.

5. The sensor, as set forth in claim 1, comprising a calibration element adapted to provide at least one signal related to at least one physical characteristic of the sensor.

6. The sensor, as set forth in claim 5, wherein the calibration element comprises a coded resistor or an electrically erasable programmable read-only memory.

7. The sensor, as set forth in claim 1, comprising a barrier layer defining at least part of a surface of the sensor body, wherein the barrier layer is substantially impermeable to water.

8. The sensor, as set forth in claim 1, wherein the sensor comprises an optical fiber.

9. The sensor, as set forth in claim 1, wherein the emitters and the detectors are adapted to operate in reflectance mode or transmission mode.

10. The sensor, as set forth in claim 1, wherein the sensor comprises a microneedle.

11. The sensor, as set forth in claim 1, wherein at least one emitter is adapted to emit a second wavelength related to a reference signal, and wherein at least one detector is adapted to detect the second wavelength.

12. The sensor, as set forth in claim 11, wherein the second wavelength related to a reference signal is between 3500-3600 nm.

13. A system comprising:
a sensor adapted to be coupled to a monitor, the sensor comprising:
a sensor body adapted for use associated with a patient's tissue;
one or more emitters disposed on the sensor body, wherein each emitter is adapted to emit at least one wavelength of light between 4200 nm and 4350 nm; and
one or more detectors disposed on the sensor body, wherein each detector is adapted to detect the wavelength of light, wherein each detector is positioned to have an optical distance of 200 micrometers or less with respect to at least one emitter, and wherein there are no other detectors that detect the wavelength of light disposed on the sensor body that do not have the optical distance of 200 micrometers or less with respect to at least one emitter; and
a monitor adapted to calculate dissolved carbon dioxide.

14. The system, as set forth in claim 13, wherein each emitter comprises at least one light emitting diode.

15. The system, as set forth in claim 13, wherein each detector comprises at least one photodetector.

16. The system, as set forth in claim 13, wherein the at least one wavelength of light is 4327 nanometers.

17. The system, as set forth in claim 13, comprising a calibration element adapted to provide at least one signal related to at least one physical characteristic of the sensor.

18. The system, as set forth in claim 17, wherein the calibration element comprises a coded resistor or an electrically erasable programmable read-only memory.

19. The system, as set forth in claim 13, comprising a barrier layer defining at least part of a surface of the sensor body, wherein the barrier layer is substantially impermeable to water.

20. The system, as set forth in claim 13, wherein the sensor comprises an optical fiber.

21. The system, as set forth in claim 13, wherein the emitters and the detectors are adapted to operate in reflectance mode or in transmission mode.

22. The system, as set forth in claim 13, wherein the sensor comprises a microneedle.

23. The system, as set forth in claim 13, wherein at least one emitter is adapted to emit a second wavelength related to a reference signal, and wherein at least one detector is adapted to detect the second wavelength.

24. The system, as set forth in claim 23, wherein the second wavelength related to a reference signal is between 3500-3600 nm.

25. A method of calculating dissolved carbon dioxide comprising:
emitting a light between 4200 nm and 4350 nm into a tissue with one or more emitters disposed on a sensor body;
detecting the light with one or more detectors disposed on the sensor body, wherein each detector disposed on the sensor body is positioned to have an optical distance of 200 micrometers or less with respect to at least one emitter, and wherein there are no other detectors that detect the light disposed on the sensor body that do not have the optical distance of 200 micrometers or less with respect to at least one emitter;

sending a signal related to the detected light to a processor; and determining a concentration of dissolved carbon dioxide in the tissue.

26. The method, as set forth in claim 25, comprising emitting a reference wavelength with the emitter; and detecting the reference wavelength.

* * * * *